United States Patent
Weber et al.

(10) Patent No.: US 6,413,558 B1
(45) Date of Patent: Jul. 2, 2002

(54) COMPOSITIONS, KITS, AND METHODS FOR PROVIDING AND MAINTAINING ENERGY AND METAL ALERTNESS

(75) Inventors: Regina Brigitte Weber, Steinbach; Gabrielle Blumenstein-Stahl, Hofheim, both of (DE)

(73) Assignee: The Proctor & Gamble Co., Cincinnati, OH (US)

( * ) Notice: Subject to any disclaimer, the term of this patent is extended or adjusted under 35 U.S.C. 154(b) by 0 days.

(21) Appl. No.: 09/542,156

(22) Filed: Apr. 4, 2000

Related U.S. Application Data

(60) Provisional application No. 60/144,580, filed on Jul. 19, 1999.

(51) Int. Cl.[7] .............................................. A23L 2/00
(52) U.S. Cl. ............................ 426/2; 426/72; 426/73; 426/74; 426/87; 426/590; 426/594; 424/729
(58) Field of Search ........................ 426/87, 590, 594, 426/2, 72–74, 591; 424/729

(56) References Cited

U.S. PATENT DOCUMENTS

| | | | |
|---|---|---|---|
| 3,097,947 A | | 7/1963 | Kemmerer ...................... 99/63 |
| 4,163,805 A | * | 8/1979 | Mueller ...................... 426/575 |
| 4,237,118 A | | 12/1980 | Howard ...................... 424/140 |
| 4,349,577 A | | 9/1982 | Tessler ...................... 426/590 |
| 4,497,800 A | | 2/1985 | Larson et al. ................... 514/2 |
| 4,717,579 A | * | 1/1988 | Vietti et al. .................. 426/579 |
| 5,104,676 A | | 4/1992 | Mahmoud et al. .......... 426/590 |
| 5,108,774 A | * | 4/1992 | Mills ........................... 426/599 |
| 5,114,723 A | | 5/1992 | Stray-Gundersen |
| 5,162,128 A | * | 11/1992 | Mills ........................... 426/599 |
| 5,169,671 A | * | 12/1992 | Harada ...................... 426/658 |
| 5,178,896 A | * | 1/1993 | Langner ...................... 426/590 |
| 5,209,870 A | | 5/1993 | Todd, Jr. ..................... 252/398 |
| 5,254,357 A | * | 10/1993 | Langner ...................... 426/590 |
| 5,262,162 A | | 11/1993 | Bormann et al. ......... 424/195.1 |
| 5,360,614 A | | 11/1994 | Fox et al. .................... 424/439 |
| 5,433,965 A | * | 7/1995 | Fischer et al. .............. 426/548 |
| 5,447,730 A | | 9/1995 | Greenleaf |
| 5,492,715 A | | 2/1996 | Greenland et al. .......... 426/658 |
| 5,520,948 A | | 5/1996 | Kvamme .................... 426/590 |
| 5,536,156 A | | 7/1996 | Fox et al. .................... 424/439 |
| 5,545,410 A | | 8/1996 | Fos et al. .................... 424/439 |
| 5,571,441 A | * | 11/1996 | Andon ........................ 426/648 |
| 5,597,604 A | * | 1/1997 | Chalupa ...................... 426/590 |
| 5,609,897 A | | 3/1997 | Chandler et al. ............. 426/73 |
| 5,641,531 A | | 6/1997 | Liebrecht et al. ........... 426/583 |
| 5,681,569 A | | 10/1997 | Kuznicki et al. |
| 5,776,887 A | | 7/1998 | Wibert et al. ................... 514/2 |
| 5,780,094 A | * | 7/1998 | King ........................... 426/590 |
| 5,792,754 A | | 8/1998 | Green et al. .................. 514/60 |
| 5,851,578 A | * | 12/1998 | Gandhi ....................... 426/590 |
| 5,869,118 A | * | 2/1999 | Morris ........................ 426/72 |
| 5,900,263 A | * | 5/1999 | Gics ............................ 426/87 |
| 5,919,512 A | * | 7/1999 | Montezinos ................ 426/590 |
| 5,958,484 A | * | 9/1999 | Gics ........................... 426/122 |
| 5,976,603 A | * | 11/1999 | Kota ........................... 426/590 |
| 6,004,610 A | * | 12/1999 | Wang ......................... 426/599 |
| 6,020,016 A | * | 2/2000 | Castleberry ................ 426/599 |
| 6,042,854 A | * | 3/2000 | Morris ........................ 426/72 |
| 6,071,547 A | * | 6/2000 | Schechter ................... 426/590 |
| 6,093,430 A | * | 7/2000 | Gupta ......................... 426/115 |
| 6,096,364 A | * | 8/2000 | Bok et al. ................... 426/590 |
| 6,168,821 B1 | * | 1/2001 | Castleberry ................ 426/590 |
| 6,210,722 B1 | * | 4/2001 | Wullschleger ............... 426/94 |
| 6,221,421 B1 | * | 4/2001 | Wullschleger ............. 426/590 |
| 6,224,872 B1 | * | 5/2001 | Shibuya .................... 424/195.1 |
| 6,261,589 B1 | * | 7/2001 | Pearson et al. ............ 424/439 |

FOREIGN PATENT DOCUMENTS

| | | | |
|---|---|---|---|
| EP | 0 290 054 | 5/1988 | ........ A23C/9/123 |
| EP | 0 768 043 A2 | 4/1997 | ........... A23L/1/29 |
| EP | 0 894 439 A1 | 2/1999 | ........... A23L/2/38 |
| JP | 5 4055763 | 10/1977 | |
| WO | WO 91/12734 | 9/1991 | ........... A23L/2/38 |
| WO | WO 98/04156 | 2/1998 | ......... A23L/1/236 |
| WO | WO 98/20751 | 5/1998 | ......... A23L/1/054 |

OTHER PUBLICATIONS

Anon. 1997. Food Ingredient Catalog. ADM Supermarket to the World, p. 10–11.*

Mayell, Mark. 1998. Most of us love the Boost the Comse from a Jolt of Java or a sip of Soda. Natural Health, Jul.–Aug..*

Turner, Lisa. 1999. Good 'n Plenty mood–enhancing foods. Vegetarian Times, Feb. issue.*

Janette Brand–Miller, "Carbohydrates," *Essentials Of Human Nutrition*; 1998, pp. 11–27.

F. Brouns, et al.; "Effect Of Diet Manipulation On Metabolic Changes And Performance In Competitive Cyclists," *Journal Of Human Nutrition Dietetics*, (1991), 4, 69–77.

R. Fluckiger–Isler, et al.; Dietary Components of Malt Extract Such as Maltodextrins, Proteins and Inorganic Salts Have Distinct Effects on Glucose Uptake and Glycogen Concentrations in Rats, *American Institute of Nutrition*, 1994, 1647–1653.

J. Cummings, et al., "Gastrointestinal Effects Of Food Carbohydrates," *American Journal of Clinical Nutrition*, 1995: 61 (suppl): 938S–945S.

Robert F. Bruns, "Adenosine Antagonism By Purines, Pteridines And Benzopteridines In Human Fibroblasts," *Biochemical Pharmacology*, vol. 30; pp. 325–333.

* cited by examiner

*Primary Examiner*—Carolyn Paden
(74) *Attorney, Agent, or Firm*—Kelly L. McDow-Dunham

(57) ABSTRACT

The present invention relates to compositions which provide an onset and steady maintenance of energy to the consumer, as well as kits comprising the compositions and methods of using the compositions. In particular, the compositions of the present invention comprises a select mixture of carbohydrates which provides immediate and sustained energy when consumed. The compositions may optionally, but preferably, comprise one or more bracers and/or flavanols which, in combination with the foregoing select mixture, provide sustained energy and mental alertness without nervousness or tension.

39 Claims, No Drawings

COMPOSITIONS, KITS, AND METHODS FOR PROVIDING AND MAINTAINING ENERGY AND METAL ALERTNESS

REFERENCE TO PRIORITY APPLICATION

The present application claims priority to U.S. Provisional Application Ser. No. 60/144,580, filed Jul. 19, 1999.

FIELD OF THE INVENTION

The present invention is directed to compositions which are useful as, for example, food and/or beverage compositions. The present invention is further directed to kits comprising such compositions and methods of using such compositions.

BACKGROUND OF THE INVENTION

It is common for consumers to experience a period of low energy and decreased mental alertness in the late afternoon, i.e., from about two or three hours after lunch to about dinner time. It is well established that this experience is caused by a drop in blood glucose levels. Many consumers combat this dip in energy by ingesting a beverage or a candy bar that functions as a source of sugar, such as sucrose.

Unfortunately for the consumer, these common sources of energy act too quickly and are not maintained over time. Instead, such sources tend to increase the blood glucose level quickly and excessively, followed by rapid depletion of blood glucose levels. Typically, the excessive blood glucose level triggers the body to produce insulin, which causes the glucose to be metabolized rapidly. Once the glucose is metabolized, the blood glucose level is lower than it was before the sugar-containing beverage or candy bar was consumed. This sequence of changes in the blood glucose level is experienced by the consumer as an initial "sugar high," (i.e., excess levels of glucose or sugar) followed by a "sugar crash" (i.e., depletion of glucose or sugar).

The present inventors have surprisingly discovered compositions which overcome the problems associated with the foregoing by rapidly increasing the blood glucose level to one which is appropriate to provide the required energy while avoiding the excessively high levels of blood glucose which could trigger an exaggerated insulin response. The compositions of the present invention maintain a desirable blood glucose level for an extended period of time after consumption, to provide energy and mental alertness.

SUMMARY OF THE INVENTION

The present invention relates to compositions, kits, and methods which are useful for providing and maintaining energy levels and mental alertness in a consumer. The compositions set forth herein include beverage compositions, beverage concentrates, and essentially dry compositions.

In particular, the present invention relates to beverage compositions comprising:
 (a) from about 0.1% to about 15% of one or more mono saccharides;
 (b) from about 0.1% to about 15% of one or more disaccharides;
 (c) from about 0.1% to about 15% of one or more complex carbohydrates; and
 (d) more than about 60% water.

The present invention further relates to beverage concentrates comprising:
 (a) one or more mono saccharides;
 (b) one or more disaccharides; and
 (c) one or more complex carbohydrates; and
 (d) from about 20% to about 60% water;
wherein the concentrate has a monosaccharide to complex carbohydrate ratio of from about 1:5 to about 10:1 and a monosaccharide to disaccharide ratio of from about 1:15 to about 15:1, by weight of the concentrate.

The present invention further relates to essentially dry compositions comprising:
 (a) one or more mono saccharides;
 (b) one or more disaccharides; and
 (c) one or more complex carbohydrates;
wherein the concentrate has a monosaccharide to complex carbohydrate ratio of from about 1:5 to about 10:1 and a monosaccharide to disaccharide ratio of from about 1:15 to about 15:1.

In particularly preferred embodiments of the present invention, one or more bracers and/or one or more flavanols are included in the present compositions.

DETAILED DESCRIPTION OF THE INVENTION

The present invention is directed to compositions which are useful, for example, as food and/or beverage compositions. The present invention is further directed to kits comprising such compositions and methods of using such compositions.

Publications and patents are referred to throughout this disclosure. All references cited herein are hereby incorporated by reference.

All percentages and ratios are calculated by weight unless otherwise indicated. All percentages and ratios are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for components including, but not limited to, certain carbohydrates, flavors, and other components. The inventors herein do not intend to be limited by materials under a certain trade name. Equivalent materials (e.g. those obtained from a different source under a different name or catalog (reference) number) to those referenced by trade name may be substituted and utilized in the compositions, kits, and methods herein.

In the description of the invention various embodiments and/or individual features are disclosed. As will be apparent to the ordinarily skilled practitioner, all combinations of such embodiments and features are possible and can result in preferred executions of the present invention.

The compositions, kits, and methods herein may comprise, consist essentially of, or consist of any of the elements as described herein.

As used herein, wherein the term "composition" or the like it utilized, without specific reference to a beverage composition, concentrate, or essentially dry composition, such term is meant to refer to all of the beverage compositions, concentrates, or essentially dry compositions herein.

Compositions of the Present Invention

The compositions of the present invention provide an onset and maintenance of energy and mental alertness to the consumer. Optionally and preferably, the compositions further provide satiation and/or refreshment. The present inventors have surprisingly discovered that the present compositions, which comprise a mixture of one or more monosaccharides, one or more disaccharides, one or more complex carbohydrates and, optionally, water, provide such onset and maintenance of energy and mental alertness. In particularly preferred embodiments of the present invention, one or more bracers and/or one or more flavanols are included in the present compositions. Without intending to be limited by theory, the present inventors have discovered that inclusion of one or more bracers and/or one or more flavanols (see optional components, herein below) serves to delay the glycemic response associated with ingestion of the present compositions, thus providing further maintenance of energy and mental alertness to the user.

The compositions utilized herein may be a beverage composition, typically icomprising at least about 70% water; a beverage concentrate, typically comprising from about 20% to about 70% water; and an essentially dry composition, typically comprising less than about 20% water, all by weight of the composition.

As the present inventors have discovered, the compositions of the present invention contain a balanced, complex mixture of digestible carbohydrates which provides an onset and maintenance of energy and mental alertness. The present inventors have further discovered that, in selecting effective carbohydrates and carbohydrate levels for use in the present compositions, it is important that the carbohydrates and levels thereof which are chosen allow a sufficient rate of digestion and intestinal absorption to provide a steady maintenance of glucose, which in turn provides energy and alertness to the consumer.

It has been discovered that the monosaccharide utilized herein provides immediate energy to the consumer while the disaccharide and, to a further extent the complex carbohydrate components, are hydrolyzed in the digestive tract to provide a later, and maintained, onset of energy for the consumer. As is also set forth herein, inclusion of one or more bracers and/or flavanols enhances this internal response. Accordingly, as will be discussed more particularly herein, it is a particularly preferred embodiment to provide one or more bracers and/or flavanols to the composition for optimization of the maintenance of energy and mental alertness.

The Monosaccharide

The monosaccharide utilized herein is a molecule of the general formula $C_nH_{2n}O_n$; wherein n is an integer equal to or greater than 3. The monosaccharide herein is digestible, i.e., capable of metabolism by a mammalian body. Non-limiting examples of monosaccharides which may be utilized herein include sorbitol, mannitol, erythrose, threose, ribose, arabinose, xylose, ribulose, glucose, galactose, mannose, fructose, and sorbose. Preferred monosaccharides for use herein include glucose and fructose, most preferably glucose.

The Disaccharide

The disaccharide utilized herein is a molecule of the general formula $C_nH_{2n-2}O_{n-1}$, wherein the disaccharide has 2 monosaccharide units connected via a glycosidic bond. In such formula, n is an integer equal to or greater than 3. The disaccharide herein is digestible, i.e., capable of metabolism by a mammalian body. Non-limiting examples of disaccharides which may be utilized herein include sucrose, maltose, lactitol, maltitol, maltulose, and lactose. The most preferred disaccharide for use herein is sucrose.

The Complex Carbohydrate

The complex carbohydrate utilized herein is an oligosaccharide, polysaccharide, and/or carbohydrate derivative, preferably an oligosaccharide and/or polysaccharide. As used herein, the term "oligosaccharide" means a digestible linear molecule having from 3 to 9 monosaccharide units, wherein the units are covalently connected via glycosidic bonds. As used herein, the term "polysaccharide" means a digestible (i.e., capable of metabolism by the human body) macromolecule having greater than 9 monosaccharide units, wherein the units are covalently connected via glycosidic bonds. The polysaccharides may be linear chains or branched. Preferably, the polysaccharide has from 9 to about 20 monosaccharide units. Carbohydrate derivatives, such as a polyhydric alcohol (e.g., glycerol), may also be utilized as a complex carbohydrate herein. As used herein, the term "digestible" means capable of metabolism by enzymes produced by the human body. Examples of polysaccharides not within the definitions herein include resistant starches (e.g., raw corn starches) and retrograded amyloses (e.g., high amylose corn starches) since such polysaccharides are known to be non-digestible by the human body.

Non-limiting examples of preferred complex carbohydrates include raffinoses, stachyoses, maltotrioses, maltotetraoses, glycogens, amyloses, amylopectins, polydextroses, and maltodextrins. The most preferred complex carbohydrates are maltodextrins.

Maltodextrins are a form of complex carbohydrate molecule which is several glucose units in length. Without intending to be limited by theory, since maltodextrins are hydrolyzed into glucose in the digestive tract, they may be utilized as an extended source of glucose. Maltodextrins may be spray-dried carbohydrate ingredients made by controlled hydrolysis of corn starch. As is commonly known in the art, the dextrose equivalence ("DE") of maltodextrins provides a good index of the degree of starch polymer hydrolysis. Preferred maltodextrins are those with a DE about 22 or less. Preferred maltodextrins for use herein are those with a DE of from about 15 to about 20, more preferably from about 16 to about 20.

The beverage compositions, beverage concentrates, and essentially dry compositions comprise one or more monosaccharides, one or more disaccharides, and one or more complex carbohydrates, as set forth above. The following describes such compositions in more detail.

Beverage Compositions

The present beverage compositions comprise a select mixture of simple and complex carbohydrates which has been discovered to provide an onset and maintenance of energy and mental alertness over time. As has been discovered herein, the beverage compositions described herein are particularly useful as they may provide a smooth and maintained energy to the consumer without rapid and transient peaks of glucose levels in the blood.

The present beverage compositions comprise:

(a) from about 0.1% to about 15% of one or more monosaccharides;

(b) from about 0.1% to about 15% of one or more disaccharides;

(c) from about 0.1% to about 15% of one or more complex carbohydrates; and (d) at least about 60% water.

The amount of monosaccharide utilized herein in the beverage compositions is preferably from about 0.1% to about 15%, more preferably from about 1% to about 10%, and most preferably from about 1% to about 5%. As defined herein, the total amount of monosaccharide includes any added monosaccharide as well as those naturally present in any added fruit juice, tea extract or any other component present in the compositions of the invention.

The amount of disaccharide utilized in the beverage compositions is from about 0.1% to about 15%, more preferably from about 1% to about 15%, still more preferably from about 1% to about 10%, even more preferably from about 1% to about 9%, and most preferably from about 1.5% to about 9, by weight of the composition. As defined herein, the total amount of disaccharide includes any added disaccharide as well as those naturally present in any added fruit juice, tea extract or any other component present in the compositions of the invention.

Wherein an oligosaccharide or polysaccharide is utilized as the complex carbohydrate in the present beverage compositions, the carbohydrate is used in the composition at levels from about 0.1% to about 15%, preferably from about 1% to about 10% and most preferably from about 1.5% to about 5%, by weight of the composition. Wherein use of a polyhydric alcohol is desired as the carbohydrate, from about 0.1% to about 15%, preferably from about 6% to about 10% of polyhydric alcohol will be typically utilized in the present invention. As defined herein, the total amount of complex carbohydrate includes any added complex carbohydrate as well as those naturally present in any added fruit juice, tea extract or any other component present in the compositions of the invention.

The present inventors have further discovered that the ratio of monosaccharide to complex carbohydrate is of importance as it can be adjusted to provide the onset and maintenance of energy without creating an undesirably high peak in blood glucose levels. As discovered herein, the desired ratio of monosaccharide to complex carbohydrate is from about 1:5 to about 10:1, preferably from about 1:3 to about 5:1, and most preferably from about 1:2 to about 3:1, all by weight of the composition.

The amount of water utilized in the present beverage compositions is such that it is suitable as a dilute, ready-to-drink beverage. Typically, the present beverage compositions comprise at least about 60% water, preferably at least about 70% water, still more preferably at least about 75% water, even more preferably at least about 80% water, and most preferably at least about 83% water, all by weight of the composition.

Beverage Concentrates

The present beverage concentrates comprise a select mixture of simple and complex carbohydrates which has been discovered to provide an onset and maintenance of energy and mental alertness over time. As has been discovered herein, the beverage concentrates (upon reconstitution or further dilution) described herein are particularly useful as they may provide maintained energy to the consumer without rapid and transient peaks of glucose levels in the blood.

The beverage concentrates according to the present invention may be provided as, for example, a syrup and/or an aqueous concentrate. The beverage concentrate is typically formulated to provide a drinkable beverage composition wherein the concentrate is reconstituted or diluted with water or other aqueous liquid.

The present beverage concentrates comprise:

(a) one or more monosaccharides;

(b) one or more disaccharides;

(c) one or more complex carbohydrates; and (d) from about 20% to about 60% water;

wherein the ratio of monosaccharide to complex carbohydrate is from about 1:5 to about 10:1 and wherein the ratio of monosaccharide to disaccharide is from about 1:15 to about 15:1, all by weight of the concentrate.

The amount of monosaccharide utilized herein in the beverage concentrates is preferably less than about 25%, more preferably less than about 20%, and most preferably less than about 17%, all by weight of the concentrate. As defined herein, the total amount of monosaccharide includes any added monosaccharide as well as those naturally present in any added fruit juice, tea extract or any other component present in the concentrates of the invention.

The amount of disaccharide utilized in the beverage concentrates is less than about 20%, more preferably less than about 17%, and most preferably less than about 15%, all by weight of the concentrate. As defined herein, the total amount of disaccharide includes any added disaccharide as well as those naturally present in any added fruit juice, tea extract or any other component present in the compositions of the invention.

The amount of complex carbohydrate in the in the present beverage concentrates is preferably less than about 25%, more preferably less than about 20%, and most preferably less than about 17%, all by weight of the concentrate. As defined herein, the total amount of complex carbohydrate includes any added complex carbohydrate as well as those naturally present in any added fruit juice, tea extract or any other component present in the compositions of the invention.

As with the beverage compositions described herein above, the present inventors have discovered that the ratio of monosaccharide to complex carbohydrate is of importance for the beverage concentrates as it can be adjusted to provide the onset and maintenance of energy and alertness without creating an undesirably high peak in blood glucose levels in the consumer. Similarly, the ratio of monosaccharide to disaccharide has been discovered to be important for onset and maintenance of energy. As discovered herein, in the present beverage concentrates, the desired ratio of monosaccharide to complex carbohydrate is from about 1:5 to about 10:1, preferably from about 1:3 to about 5:1, and most preferably from about 1:2 to about 3:1, all by weight of the composition. Additionally, in the present beverage concentrates, the desired ratio of monosaccharide to disaccharide is from about 1:15 to about 15:1, preferably from about 1:7 to about 7:1, and most preferably from about 1:3 to about 3:1, all by weight of the concentrate.

The amount of water utilized in the present beverage concentrates is such that it is suitable as a concentrate, typically in the form of a syrup or aqueous concentrate, which is ready-to-drink upon further dilution with water or other aqueous liquid. Typically, the present beverage concentrates comprise from about 20% to about 60% water, preferably from about 20% to about 50% water, and most preferably from about 20% to about 40% water, all by weight of the concentrate.

Essentially Dry Compositions

The present essentially dry compositions also comprise a select mixture of simple and complex carbohydrates which has been discovered to provide an onset and maintenance of energy and alertness over time. As has been discovered herein, the essentially dry beverage compositions (upon reconstitution or further dilution) described herein are particularly useful as they may provide maintained energy to the consumer without rapid and transient peaks of glucose levels in the blood.

The essentially dry beverage compositions are typically in, for example, powder, granule, or tablet form. The essentially dry beverage compositions are may be diluted with water, or other aqueous fluid, or may be incorporated into other solids such as, for example, bars (e.g., cereal bars, breakfast bars, energy bars, and nutritional bars). Wherein the essentially dry composition is consumed, either as a beverage or solid food, the consumer may experience maintained energy over time rather than rapid, transient glucose peaks typically associated with sugar-containing beverages and foods.

The present essentially dry compositions comprise:
(a) one or more monosaccharides;
(b) one or more disaccharides;
(c) one or more complex carbohydrates; and
(d) less than about 20% water;
wherein the ratio of monosaccharide to complex carbohydrate is from about 1:5 to about 10:1 and wherein the ratio of monosaccharide to disaccharide is from about 1:15 to about 15:1, all by weight of the composition.

The amount of monosaccharide utilized herein in the present essentially dry compositions is preferably from about 10% to about 75%, more preferably from about 20% to about 50%, and most preferably from about 25% to about 40%, all by weight of the composition. As defined herein, the total amount of monosaccharide includes any added monosaccharide as well as those naturally present in any added component present in the compositions of the invention.

The amount of disaccharide utilized in the essentially dry compositions is preferably from about 10% to about 75%, more preferably from about 20% to about 50%, and most preferably from about 25% to about 40%, all by weight of the composition. As defined herein, the total amount of disaccharide includes any added disaccharide as well as those naturally present in any added component present in the compositions of the invention.

The amount of complex carbohydrate in the present essentially dry compositions is preferably from about 5% to about 60%, more preferably from about 10% to about 40%, and most preferably from about 15% to about 30%, all by weight of the composition. As defined herein, the total amount of complex carbohydrate includes any added complex carbohydrate as well as those naturally present in any added component present in the compositions of the invention.

As with the beverage compositions described herein above, the present inventors have discovered that the ratio of monosaccharide to complex carbohydrate is of importance for the essentially dry compositions as it can be adjusted to provide the onset and maintenance of energy without creating an undesirably high peak in blood glucose levels in the consumer. Similarly, the ratio of monosaccharide to disaccharide has been discovered to be important for onset and maintenance of energy. As discovered herein, in the present essentially dry compositions, the desired ratio of monosaccharide to complex carbohydrate is from about 1:5 to about 10:1, preferably from about 1:3 to about 5:1, and most preferably from about 1:2 to about 3:1, all by weight of the composition. Additionally, in the present essentially dry compositions, the desired ratio of monosaccharide to disaccharide is from about 1:15 to about 15:1, preferably from about 1:7 to about 7:1, and most preferably from about 1:3 to about 3:1, all by weight of the composition.

The amount of water utilized in the present essentially dry compositions is typically less than about 20%, preferably less than about 10%, more preferably less than about 5%, and most preferably less than about 3%, all by weight of the composition.

Optional Components of the Present Compositions

The compositions of the present invention may comprise additional optional components to enhance, for example, their performance in providing energy, mental alertness, organoleptic properties, and nutritional profile. For example, one or more bracers, flavanols, milk base solids, soluble fibers, non-caloric sweeteners, nutrients, flavoring agents, coloring agents, preservatives, emulsifiers, oils, carbonation components, and the like may be included in the compositions herein. Such optional components may be dispersed, solubilized, or otherwise mixed into the present compositions. These components may be added to the compositions herein provided they do not substantially hinder the properties of the beverage composition, particularly the provision of energy and mental alertness. Non-limiting examples of optional components suitable for use herein are given below.

Bracers

One or more bracers may be included in the present invention to provide the consumer an additional onset and maintenance of energy, and thus alertness, without the tension or nervousness normally associated with bracers in typical beverage compositions. Without intending to be limited by theory, the present inventors have discovered that inclusion of one or more bracers serves to delay the glycemic response associated with ingestion of the present compositions, thus providing further maintenance of energy to the user. Because one or more bracers will contribute to the onset, and particularly maintenance of energy wherein the composition is ingested, it is a particularly preferred embodiment of the present invention to include one or more bracers.

As is commonly known in the art, bracers can be obtained by extraction from a natural source or can be synthetically produced. Non-limiting examples of bracers include methylxanthines, e.g., caffeine, theobromine, and theophylline. Additionally, numerous other xanthine derivatives have been isolated or synthesized, which may be utilized as a bracer in the compositions herein. See e.g., Bruns, *Biochemical Pharmacology*, Vol. 30, pp. 325–333 (1981) which describes, inter alia, xanthine, 9-methyl xanthine, 7-methyl xanthine, 3-methyl xanthine, 3,7-dimethyl xanthine, 8-chloromethyl-3,7-dimethyl xanthine, 8-hydroxymethyl-3,7-dimethyl xanthine, 3,7-diethyl xanthine, 3,7-bis-(2-hydroxyethyl) xanthine, 3-propyl-7-(dimethylaminoethyl) xanthine, 1-methyl xanthine, 1,9-dimethyl xanthine, 1-methyl-8-methylthio xanthine, 8-phenyl-1-methyl xanthine, 1,7-dimethyl xanthine, 1,7-dimethyl-8-oxo xanthine, 1,3-dimethyl xanthine, 1,3,9-trimethyl xanthine, 8-fluoro theophylline, 8-chloro theophylline, 8-bromo theophylline, 8-thio theophylline, 8-methylthio theophylline, 8-ethylthio theophylline, 8-nitro theophylline, 8-methylamino theophylline, 8-dimethylamino theophylline, 8-methyl theophylline, 8-ethyl theophylline, 8-propyl theophylline, 8-cyclopropyl theophylline, theophylline-8-propionate (ethyl ester), 8-benzyl theophylline, 8-cyclopentyl theophylline, 8-cyclohexyl theophylline, 8-(3-indolyl) theophylline, 8-phenyl theophylline, 9-methyl-8-phenyl theophylline, 8-(p-chlorophenyl) theophylline, 8-(p-bromophenyl) theophylline, 8-(p-methoxyphenyl) theophylline, 8-(p-nitrophenyl) theophylline, 8-(p-dimethylaminophenyl) theophylline, 8-(p-methylphenyl) theophylline, 8-(3,4-dichlorophenyl) theophylline, 8-(m-nitrophenyl) theophylline, 8-(o-nitrophenyl) theophylline, 8-(o-carboxyphenyl) theophylline, 8-(1-naphthyl) theophylline, 8-(2,6-dimethyl-4-hydroxyphenyl) theophylline, 7-methoxy-8-phenyl theophylline, 1,3,7-trimethyl xanthine, S-chloro caffeine, S-oxo caffeine, S-methoxy caffeine, S-methylamino caffeine, 8-diethylamino caffeine, 8-ethyl caffeine, 7-ethyl theophylline, 7-(2-chloroethyl) theophylline, 7-(2-hydroxyethyl) theophylline, 7-(carboxymethyl) theophylline, 7-(carboxymethyl) theophylline (ethyl ester), 7-(2-hydroxypropyl) theophylline, 7-(2,3-dihydroxypropyl) theophylline, 7-β-D-ribofuranosyl theophylline, 7-(glycero-pent-2-enopyranosyl) theophylline, 7-phenyl theophylline, 7,8-diphenyl theophylline, 1-methyl-3,7-diethyl xanthine, 1-methyl-3-isobutyl xanthine, 1-ethyl-3,7-dimethyl xanthine, 1,3-diethyl xanthine, 1,3,7-triethyl xanthine, 1-ethyl-3-propyl-7-butyl-8-methyl xanthine, 1,3-dipropyl xanthine, 1,3-diallyl xanthine, 1-butyl-3,7-dimethyl xanthine, 1-hexyl-3,7-dimethyl xanthine, and 1-(5-oxohexyl)-3,7-dimethyl xanthine.

Additionally, one or more of these bracers are present in, for example, coffee, tea, kola nut, cacao pod, mate', yaupon, guarana paste, and yoco. Natural plant extracts are the preferred sources of bracers as they may contain other compounds that delay the bioavailability of the bracer thus they may provide mental refreshment and alertness without tension or nervousness.

The most preferred methylxanthine is caffeine. Caffeine may be obtained from the aforementioned plants and their waste or, alternatively, may be synthetically prepared. Preferred botanical sources of caffeine which may be utilized as a complete or partial source of caffeine include green tea, guarana, mate', black tea, cola nuts, cocoa, and coffee. As used herein, green tea, guarana, coffee, and mate' are the most preferred botanical sources of caffeine, most preferably green tea, guarana, and coffee. Mate' may have the additional benefit of an appetite suppressing effect and may be included for this purpose as well. The total amount of caffeine, in any embodiment of the present invention, includes the amount of caffeine naturally present in the tea extract, flavoring agent, botanical and any other components, as well as any added caffeine.

Any bracer utilized herein is preferably present in physiologically relevant amounts, which means that the sources used in the practice of this invention provide a safe and effective quantity to achieve the desired mental alertness.

Wherein a bracer is utilized in the present beverage compositions, such compositions will preferably comprise from about 0.0005% to about 1%, more preferably from about 0.003% to about 0.5%, still more preferably from about 0.003% to about 0.2%, even more preferably from about 0.005% to about 0.05%, and most preferably from about 0.005% to about 0.02% of a bracer, by weight of the composition. Of course, as the skilled artisan will comprehend, the actual amount of bracer added will depend its biological effect, for example, effect of mental alertness on the consumer.

Wherein a bracer is utilized in the present beverage concentrates, such concentrates will preferably comprise from about from about 0.004% to about 1.4%, more preferably from about 0.02% to about 0.7%, and most preferably from about 0.03% to about 0.2% of the bracer, by weight of the concentrate.

Wherein a bracer is incorporated an essentially dry composition of the present invention, the composition preferably comprises from about 0.004% to about 1.4%, more preferably from about 0.02% to about 0.7%, and most preferably from about 0.03% to about 0.2% of the bracer, by weight of the essentially dry composition.

In all of the present compositions, the total amount of bracer includes any added bracer as well as any bracer naturally present in any other component of the present invention.

Flavanols

Another optional, but particularly preferable component of the present invention are one or more flavanols. Without intending to be limited by theory, the present inventors have discovered that inclusion of one or more flavanols serves to delay the glycemic response associated with ingestion of the present compositions, thus providing further maintenance of energy to the user. Because one or more flavanols will contribute to the onset, and particularly maintenance of energy wherein the composition is ingested, it is a particularly preferred embodiment of the present invention to include one or more flavanols.

Flavanols are natural substances present in a variety of plants (e.g., fruits, vegetables, and flowers). The flavanols which may be utilized in the present invention can be extracted from, for example, fruit, vegetables, green tea or other natural sources by any suitable method well known to those skilled in the art. For example, extraction with ethyl acetate or chlorinated organic solvents is a common method to isolate flavanols from green tea. Flavanols may be extracted from either a single plant or mixtures of plants. Many fruits, vegetables, and flowers contain flavanols but to a lesser degree relative to green tea. Plants containing flavanols are known to those skilled in the art. Examples of the most common flavanols which are extracted from tea plants and other members of the *Catechu gambir* (Uncaria family) include, for example, catechin, epicatechin, gallocatechin, epigallocatechin, epicatechin gallate, and epigallocatechin gallate.

The flavanols utilized in all compositions of the present invention can be in the form of a tea extract. The tea extract can be obtained from the extraction of unfermented teas, fermented teas, partially fermented teas, and mixtures thereof. Preferably, the tea extracts are obtained from the extraction of unfermented and partially fermented teas. The most preferred tea extracts are obtained from green tea. Both hot and cold extracts can be used in the present invention. Suitable methods for obtaining tea extracts are well known. See e.g., Ekanavake, U.S. Pat. No. 5,879,733, issued Mar. 9, 1999; Tsai, U.S. Pat. No. 4,935,256, issued June, 1990; Lunder, U.S. 4,680,193, issued July, 1987; and Creswick U.S. Pat. No. 4,668,525, issued May 26, 1987.

The preferred source of flavanols in the compositions of the present invention is green tea. Wherein green tea, and in particular the flavanols present in green tea, are incorporated into the beverage, the present inventors have discovered that the flavanols are at least partially responsible for delaying the bioavailability of bracers, which contributes to the reduction and/or elimination of nervousness and tension typically associated with such bracers.

Alternatively, these same flavanols may be prepared by synthetic or other appropriate chemical methods and incorporated into the present compositions. Flavanols, including catechin, epicatechin, and their derivatives are commercially available.

The amount of flavanols in the beverage compositions of the present invention can vary. However, wherein one or more flavanols are utilized, preferably from about 0.001% to about 5%, more preferably from about 0.001% to about 2%, even more preferably from about 0.01% to about 1%, and most preferably from about 0.01% to about 0.05% of one or more flavanols is utilized, by weight of the composition. Additionally, wherein a bracer is utilized in the present compositions, the ratio of bracer (e.g., caffeine) to flavanol is preferably from about 1:0.5 to about 1:30, more preferably from about 1:1 to about 1:30,even more preferably from about 1:1 to about 1:10, and most preferably from about 1:1to about 1:4, by weight of the beverage composition.

Wherein one or more flavanols is utilized in the present beverage concentrates or in the essentially dry compositions, the amount of flavanol present in the beverage concentrate or essentially dry composition is preferably at least from about 0.001% to about 10%, more preferably from about 0.01% to about 7%, even more preferably from about 0.05% to about 2%, and most preferably from about 0.07% to about 0.4% of flavanol, by weight of the concentrate or essentially dry composition. Additionally, wherein a bracer is utilized in the present concentrates or essentially dry compositions, the ratio of bracer (e.g., caffeine) to flavanol is preferably from about 1:0.5 to about 1:30, more preferably from about 1:1 to about 1:30, even more preferably from about 1:1 to about 1:10, and most preferably from about 1:1 to about 1:4, by weight of the concentrate or essentially dry composition.

In all of the embodiments of the present invention, the total amount of flavanols includes any added flavanols as well as any flavanols naturally present in any other component of the present invention.

Milk Base Solids

One or more milk base solids may also optionally be included in the compositions of the present invention to provide, for example, satiation and refreshment. As used herein, milk base means milk from one or more mammals or a plant-derived milk, and includes, for example, fermented milk, lactic acid beverages obtained by lactic acid fermentation or otherwise acidified, sterilized milk base, liquid milk, and milk products such as skim milk powder or whole milk powder or other powdered forms of milk. As used herein, milk base solids means the solids content or dry matter of milk base.

Wherein one or more milk base solids is utilized, the desired total level of milk base solids, calculated on a milk solids basis for the compositions of the present invention, is from about 0.001% to about 15%, preferably from about 0.005% to about 10%, and most preferably from about 0.1% to about 5%. The total amount of milk base solids includes any added milk base solid as well as any milk base solid naturally present in any other component of the present invention.

Soluble Fibers

One or more soluble fibers may also optionally be included in the compositions of the present invention to provide, for example, satiation and refreshment, and/or nutritive benefits. Soluble dietary fibers are a form of carbohydrates which cannot be metabolized by the enzyme system produced by the human body and which pass through the small intestine without being hydrolyzed (and, thus, are not included within the definition of complex carbohydrate herein). Without intending to be limited by theory, since soluble dietary fibers swell in the stomach, they slow down gastric emptying thus prolonging the retention of nutrients in the intestine which results in a feeling of satiation.

Soluble fibers which can be used singularly or in combination in all embodiments of the present invention include but are not limited to pectins, psyllium, guar gum, xanthan gum, alginates, gum arabic, fructo-oligosaccharides, inulin, agar, and carrageenan. Preferred among these soluble fibers are at least one of guar gum, xanthan, and carrageenan, most preferably at least one of guar gum and xanthan. These soluble fibers may also serve as stabilizing agents in the various embodiments of this invention.

Particularly preferred soluble fibers for use herein are glucose polymers, preferably those which have branched chains. Preferred among these soluble fibers is one marketed under the trade name Fiβersol2, commercially available from Matsutani Chemical Industry Co., Itami City, Hyogo, Japan.

Pectin and fructo-oligosaccharides are also preferred soluble fibers herein. Even more preferably, pectin and fructo-oligosaccharides are used in combination. The preferred ratio of pectin to fructo-oligosaccharide is from about 3:1 to about 1:3, by weight of the composition. The preferred pectins have a degree of esterification higher than about 65%.

The preferred fructo-oligosaccharides are a mixture of fructo-oligosaccharides composed of a chain of fructose molecules linked to a molecule of sucrose. Most preferably, they have a nystose to kestose to fructosyl-nystose ratio of about 40:50:10, by weight of the composition. Preferred fructo-oligosaccharides may be obtained by enzymatic action of fructosyltransferase on sucrose such as those which are, for example, commercially available from Beghin-Meiji Industries, Neuilly-sur-Seine, France.

Preferred pectins are obtained by hot acidic extraction from citrus peels and may be obtained, for example, from Danisco Co., Braband, Denmark.

Wherein a soluble fiber is utilized, the desired total level of soluble dietary fiber for the compositions of the present invention is from about 0.01% to about 15%, preferably from about 0.1% to about 5%, more preferably from about 0.1% to about 3%, and most preferably from about 0.2% to about 2%, by weight of the composition. The total amount of soluble dietary fiber includes any added soluble dietary fiber as well as any soluble dietary fiber naturally present in any other component of the present invention.

Wherein a soluble fiber is utilized herein, the ratio of the total carbohydrates to total soluble fiber in the present compositions is preferably from about 100:1 to about 1:1, more preferably from about 60:1 to about 10:1 and most preferably from about 40:1 to about 10:1.

Wherein a milk base solid (see herein above) and soluble fiber is utilized, and in order for the embodiments of the present invention to be optimally satiating and refreshing, the soluble fiber to milk base solids ratio is, preferably, from about 5:1 to about 1:20, more preferably from about 5:1 to about 1:10 and most preferably from about 2:1 to about 1:6, by weight of the composition.

Non-Caloric Sweeteners

Effective levels of non-caloric sweeteners may optionally be used in the compositions of the present invention to further sweeten such compositions. Non-limiting examples of non-caloric sweeteners include aspartame, saccharine, cyclamates, acesulfame K, L-aspartyl-L-phenylalanine lower alkyl ester sweeteners, L-aspartyl-D-alanine amides such as, for example, those disclosed in Brennan et al., U.S. Pat. No. 4,411,925, issued 1983, L-aspartyl-D-serine amides such as, for example, those disclosed in Brennan et al., U.S. Pat. No. 4,399,163, issued 1983, L-aspartyl-hydroxymethyl alkane amide sweeteners such as, for example, those disclosed in Brand, U.S. Pat. No. 4,338,346, issued 1982, L-aspartyl-1-hydroxyethylalkane amide sweeteners such as, for example, those disclosed in Rizzi U.S. Pat. No. 4,423,029, issued 1983, glycyrrhizins, and synthetic alkoxy aromatics. Lo Han Guo juice, stevioside, and sucralose. Aspartame and acesulfame-K are the most preferred non-caloric sweeteners utilized herein, and may be utilized alone or in combination.

Wherein one or more non-caloric sweeteners are utilized herein, the total non-caloric sweetener is preferably utilized at levels from about 0.0001% to about 5%, more preferably from about 0.001% to about 3%, still more preferably from about 0.005% to about 2%, even more preferably from about 0.01% to about 1%, and most preferably from about 0.01% to about 0.05%, by weight of the composition.

Nutrients

The compositions herein are optionally, but preferably, fortified with one or more nutrients, especially one or more vitamins and/or minerals. The U.S. Recommended Daily Intake (USRDI) for vitamins and minerals are defined and set forth in the Recommended Daily Dietary Allowance-Food and Nutrition Board, National Academy of Sciences-National Research Council.

Unless otherwise specified herein, wherein a given mineral is present in the composition, the composition typically comprises at least about 1%, preferably at least about 5%, more preferably from about 10% to about 200%, even more preferably from about 40% to about 150%, and most preferably from about 60% to about 125% of the USRDI of such mineral. Unless otherwise specified herein, wherein a given mineral is present in the composition, the composition comprises at least about 1%, preferably at least about 5%, more preferably from about 10% to about 200%, even more preferably from about 20% to about 150%, and most preferably from about 25% to about 120% of the USRDI of such vitamin.

Non-limiting examples of such vitamins and minerals, include niacin, thiamin, folic acid, pantothenic acid, biotin, vitamin A, vitamin C, vitamin $B_2$, vitamin $B_3$, vitamin $B_6$, vitamin $B_{12}$, vitamin D, vitamin E, vitamin K, iron, zinc, copper, calcium, phosphorous, iodine, chromium, molybdenum, and fluoride. Preferably, wherein a vitamin or mineral is utilized the vitamin or mineral is selected from niacin, thiamin, folic acid, iodine, vitamin A, vitamin C, vitamin $B_6$, vitamin $B_{12}$, vitamin D, vitamin E, iron, zinc, and calcium. A particularly preferred mineral for use herein is calcium. Preferably, at least one vitamin is selected from vitamin C, vitamin $B_6$, vitamin $B_{12}$, vitamin E, pantothenic acid, niacin, and biotin. Also preferably, the composition comprises vitamin C and one or more other vitamins selected from vitamin $B_6$, vitamin $B_{12}$, vitamin E, pantothenic acid, niacin, and biotin. In an especially preferred embodiment of the present invention, a composition comprises vitamin C, vitamin $B_6$, vitamin $B_{12}$, vitamin E, pantothenic acid, niacin, and biotin.

Commercially available vitamin A sources may also be included in the present compositions. As used herein, "vitamin A" includes, but is not limited to, vitamin A (retinol), β-carotene, retinol palmitate, and retinol acetate. The vitamin A may be in any form, for example, an oil, beadlets, or encapsulated. Wherein vitamin A is present in the compositions herein, the product comprises at least about 1%, preferably at least about 5%, more preferably from about 10% to about 200%, even more preferably from about 15% to about 150%, and most preferably from about 20% to about 120% of the USRDI of such vitamin. Wherein vitamin A is present in the compositions herein, it is especially preferred to include about 25% of the USRDI of vitamin A. The quantity of vitamin A to be added is dependent on processing conditions and the amount of vitamin A deliver desired after storage. Preferably, wherein vitamin A is included within the present compositions, the compositions comprise from about 0.0001% to about 0.2%, more preferably from about 0.0002% to about 0.12%, also preferably from about 0.0003% to about 0.1%, even more preferably from about 0.0005% to about 0.08%, and most preferably from about 0.001% to about 0.06% of vitamin A, by weight of the product.

Commercially available sources of vitamin $B_2$ (also known as riboflavin) may be utilized in the present compositions. Wherein vitamin $B_2$ is present in the compositions herein, the product comprises at least about 1%, preferably at least about 5%, more preferably from about 5% to about 200%, even more preferably from about 10% to about 150%, and most preferably from about 10% to about 120% of the USRDI of such vitamin. Wherein vitamin $B_2$ is present in the compositions herein, it is especially preferred to include from about 15% to about 35% of the USRDI of vitamin $B_2$.

Commercially available sources of vitamin C can be used herein. Encapsulated ascorbic acid and edible salts of ascorbic acid can also be used. Wherein vitamin C is present in the compositions herein, the product comprises at least about 1%, preferably at least about 5%, more preferably from about 10% to about 200%, even more preferably from about 20% to about 150%, and most preferably from about 25% to about 120% of the USRDI of such vitamin. Wherein vitamin C is present in the compositions herein, it is especially preferred to include about 100% of the USRDI of vitamin C. The quantity of vitamin C to be added is dependent on processing conditions and the amount of vitamin C deliver desired after storage. Preferably, wherein vitamin C is included within the present compositions, the compositions comprise from about 0.005% to about 0.2%, more preferably from about 0.01% to about 0.12%, also preferably from about 0.02% to about 0.1%, even more preferably from about 0.02% to about 0.08%, and most preferably from about 0.03% to about 0.06% of vitamin C, by weight of the product.

Commercial sources of iodine, preferably as an encapsulated iodine may be utilized herein. Other sources of iodine include iodine-containing salts, e.g., sodium iodide, potassium iodide, potassium iodate, sodium iodate, or mixtures thereof. These salts may be encapsulated.

Nutritionally supplemental amounts of other vitamins which may be incorporated herein include, but are not limited to, vitamins $B_6$ and $B_{12}$, folic acid, niacin, pantothenic acid, folic acid, vitamin D, and vitamin E. Wherein the product comprises one of these vitamins, the product preferably comprises at least 5%, preferably at least 25%, and most preferably at least 35% of the USRDI for such vitamin.

Minerals which may optionally be included in the compositions herein are, for example, magnesium, zinc, iodine, iron, and copper. Any soluble salt of these minerals suitable for inclusion edible compositions can be used, for example, magnesium citrate, magnesium gluconate, magnesium sulfate, zinc chloride, zinc sulfate, potassium iodide, copper sulfate, copper gluconate, and copper citrate.

Calcium is a particularly preferred mineral for use in the present invention. Preferred sources of calcium include, for example, amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium titrate, calcium gluconate, calcium realate, calcium tantrate, and calcium lactate, and in particular calcium citrate-malate. The form of calcium citratemalate is described in, e.g., Mehansho et al., U.S. Pat. No. 5,670,344, issued Sep. 23, 1997; Diehl et al., U.S. Pat. No. 5,612,026, issued Mar. 18, 1997; Andon et al., U.S. Pat. No. 5,571,441, issued Nov. 5, 1996; Meyer et al., U.S. Pat. No. 5,474,793, issued Dec. 12, 1995; Andon et al., U.S. Pat. No. 5,468,506, issued Nov. 21, 1995; Burkes et al., U.S. Pat. No. 5,445,837, issued Aug. 29, 1995; Dake et al., U.S. Pat. No. 5,424,082, issued Jun. 13, 1995; Burkes et al., U.S. Pat. No. 5,422,128, issued Jun. 6, 1995; Burkes et al., U.S. Pat. No. 5,401,524, issued Mar. 28, 1995; Zuniga et al., U.S. Pat. No. 5,389,387, issued Feb. 14, 1995; Jacobs U.S. Pat. No. 5,314,919, issued May 24, 1994; Saltman et al., U.S. Pat. No. 5,232,709, issued Aug. 3, 1993; Camden et al., U.S. Pat. No. 5,225,221, issued Jul. 6, 1993; Fox et al., U.S. Pat. No. 5,215,769, issued Jun. 1, 1993; Fox et al., U.S. Pat. No. 5,186,965, issued Feb. 16, 1993; Saltman et al., U.S. Pat. No. 5,151,274, issued Sep. 29, 1992; Kochanowski, U.S. Pat. No. 5,128,374, issued Jul. 7, 1992; Mehansho et al., U.S. Pat. No. 5,118,513, issued Jun. 2, 1992; Andon et al., U.S. Pat. No. 5,108,761, issued Apr. 28, 1992; Mehansho et al., U.S. Pat. No. 4,994,283, issued Feb. 19, 1991; Nakel et al., U.S. Pat. No. 4,786,510, issued Nov. 22, 1988; and Nakel et al., U.S. Pat. No. 4,737,375, issued Apr. 12, 1988. Preferred compositions of the present invention will comprise from about 0.01% to about 0.5%, more preferably from about 0.03% to about 0.2%, even more preferably from about 0.05% to about 0.15%, and most preferably from about 0.1% to about 0.15% of calcium, by weight of the product.

Iron may also be utilized in the compositions and methods of the present invention. Acceptable forms of iron are well-known in the art. The amount of iron compound incorporated into the product will vary widely depending upon the level of supplementation desired in the final product and the targeted consumer. Iron fortified compositions of the present invention typically contain from about 5% to about 100%, preferably from about 15% to about 50%, and most preferably about 20% to about 40% of the USRDI for iron.

Ferrous iron is typically better utilized by the body than ferric iron. Highly bioavailable ferrous salts that can be used in the ingestible compositions of the present invention are ferrous sulfate, ferrous fumarate, ferrous succinate, ferrous gluconate, ferrous lactate, ferrous tartarate, ferrous citrate, ferrous amino acid chelates, as well as mixtures of these ferrous salts. While ferrous iron is typically more bioavailable, certain ferric salts can also provide highly bioavailable sources of iron. Highly bioavailable ferric salts that can be used in the food or beverage compositions of the present invention are ferric saccharate, ferric ammonium citrate, ferric citrate, ferric sulfate, as well as mixtures of these ferric salts. Combinations or mixtures of highly bioavailable ferrous and ferric salts can be used in these edible mixes and ready-to-serve beverages. The preferred sources of highly bioavailable iron are ferrous fumarate and ferrous amino acid chelates.

Ferrous amino acid chelates particularly suitable as highly bioavailable iron sources for use in the present invention are those having a ligand to metal ratio of at least 2:1. For example, suitable ferrous amino acid chelates having a ligand to metal mole ratio of two are those of formula:

where L is an alpha amino acid, dipeptide, tripeptide, or quadrapeptide ligand. Thus, L can be any ligand which is a naturally occurring alpha amino acid selected from alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, and valine; or dipeptides, tripeptides, or quadrapeptides formed by any combination of these alpha amino acids. See eg., Ashmead et al., U.S. Pat. No. 4,863,898, issued Sep. 5, 1989; Ashmead, U.S. Pat. No. 4,830,716, issued May 16, 1989; and Ashmead, U.S. Pat. No. 4,599,152, issued Jul. 8, 1986, all of which are incorporated by reference. Particularly preferred ferrous amino acid chelates are those where the reacting ligands are glycine, lysine, and leucine. Most preferred is the ferrous amino acid chelate sold under the mark Ferrochel® (Albion Laboratories, Salt Lake City, Utah) wherein the ligand is glycine.

In addition to these highly bioavailable ferrous and ferric salts, other sources of bioavailable iron can be included in the food and beverage compositions of the present invention. Other sources of iron particularly suitable for fortifying compositions of the present invention included certain iron-sugar-carboxylate complexes. In these iron-sugar-carboxylate complexes, the carboxylate provides the counterion for the ferrous (preferred) or ferric iron. The overall synthesis of these iron-sugar-carboxylate complexes involves the formation of a calcium-sugar moiety in aqueous media (for example, by reacting calcium hydroxide with a sugar, reacting the iron source (such as ferrous ammonium sulfate) with the calcium-sugar moiety in aqueous media to provide an iron-sugar moiety, and neutralizing the reaction system with a carboxylic acid (the "carboxylate counterion") to provide the desired iron-sugar- carboxylate complex. Sugars that can be used to prepare the calcium-sugar moiety include any of the ingestible saccharidic materials, and mixtures thereof, such as glucose, sucrose and fructose, mannose, galactose, lactose, maltose, and the like, with sucrose and fructose being the more preferred. The carboxylic acid providing the "carboxylate counterion" can be any ingestible carboxylic acid such as citric acid, malic acid tartaric acid, lactic acid, succinic acid, propionic acid, etc., as well as mixtures of these acids.

These iron-sugar-carboxylate complexes can be prepared in the manner described in, e.g., Nakel et al., U.S. Pat. Nos. 4,786,510 and 4,786,518, issued Nov. 22, 1988, both of which are incorporated by reference. These materials are referred to as "complexes", but they may exist in solution as complicated, highly hydrated, protected colloids; the term "complex" is used for the purpose of simplicity.

Zinc may also be utilized in the compositions and methods of the present invention. Acceptable forms of zinc are well-known in the art. Zinc fortified compositions of the present invention typically contain from about 5% to about 100%, preferably from about 15% to about 50%, and most preferably about 25% to about 45% of the USRDI for zinc. The zinc compounds which can be used in the present invention can be in any of the commonly used forms such as, e.g., zinc sulfate, zinc chloride, zinc acetate, zinc gluconate, zinc ascorbate, zinc citrate, zinc aspartate, zinc picolinate, amino acid chelated zinc, and zinc oxide. Zinc gluconate and amino acid chelated zinc are particularly preferred.

Flavoring Agents

One or more flavoring agents are recommended for the embodiments of the present invention in order to enhance their palatability. Any natural or synthetic flavor agent can be used in the present invention. For example, one or more botanical and/or fruit flavors may be utilized herein. As used herein, such flavors may be synthetic or natural flavors.

Particularly preferred fruit flavors are exotic and lactonic flavors such as, for example, passion fruit flavors, mango flavors, pineapple flavors, cupuacu flavors, guava flavors, cocoa flavors, papaya flavors, peach flavors, and apricot flavors. Besides these flavors, a variety of other fruit flavors can be utilized such as, for example, apple flavors, citrus flavors, grape flavors, raspberry flavors, cranberry flavors, cherry flavors, and the like. These fruit flavors can be derived from natural sources such as fruit juices and flavor oils, or may alternatively be synthetically prepared.

Preferred botanical flavors include, for example, tea (preferably black and green tea, most preferably green tea), aloe vera, guarana, ginseng, ginkgo, hawthorn, hibiscus, rose hips, chamomile, peppermint, fennel, ginger, licorice, lotus seed, schizandra, saw palmetto, sarsaparilla, safflower, St. John's Wort, curcuma, cardimom, nutmeg, cassia bark, buchu, cinnamon, jasmine, haw, chrysanthemum, water chestnut, sugar cane, lychee, bamboo shoots, vanilla, coffee, and the like. Preferred among these is tea, guarana, ginseng, ginko, and coffee. In particular, the combination of tea flavors, preferably green tea or black tea flavors (preferably green tea), optionally together with fruit flavors has an appealing taste. In another preferred embodiment, coffee is included within the present compositions. A combination of green tea and coffee in the present compositions is often preferred.

The flavor agent can also comprise a blend of various flavors. If desired, the flavor in the flavoring agent may be formed into emulsion droplets which are then dispersed in the beverage composition or concentrate. Because these droplets usually have a specific gravity less than that of water and would therefore form a separate phase, weighting agents (which can also act as clouding agents) can be used to keep the emulsion droplets dispersed in the beverage composition or concentrate. Examples of such weighting agents are brominated vegetable oils (BVO) and resin esters, in particular the ester gums. See L. F. Green, Developments in Soft Drinks Technology, Vol. 1, Applied Science Publishers Ltd., pp. 87–93 (1978) for a further description of the use of weighting and clouding agents in liquid beverages. Typically the flavoring agents are conventionally available as concentrates or extracts or in the form of synthetically produced flavoring esters, alcohols, aldehydes, terpenes, sesquiterpenes, and the like.

Coloring Agent

Small amounts of one or more coloring agents may be utilized in the compositions of the present invention. FD&C dyes (e.g., yellow #5, blue #2,red #40) and/or FD&C lakes are preferably used. By adding the lakes to the other powdered ingredients, all the particles, in particular the colored iron compound, are completely and uniformly colored and a uniformly colored beverage mix is attained. Preferred lake dyes which may be used in the present invention are the FDA-approved Lake, such as Lake red #40, yellow #6, blue #1, and the like. Additionally, a mixture of FD&C dyes or a FD&C lake dye in combination with other conventional food and food colorants may be used. Riboflavin and β-carotene may also be used. Additionally, other natural coloring agents may be utilized including, for example, fruit, vegetable, and/or plant extracts such as grape, black currant, aronia, carrot, beetroot, red cabbage, and hibiscus.

The amount of coloring agent used will vary, depending on the agents used and the intensity desired in the finished product. The amount can be readily determined by one skilled in the art. Generally, if utilized, the coloring agent should be present at a level of from about 0.0001% to about 0.5%, preferably from about 0.001% to about 0.1%, and most preferably from about 0.004% to about 0.1%, by weight of the composition.

Preservatives

Optionally, one or more preservatives may additionally be utilized herein. Preferred preservatives include, for example, sorbate, benzoate, and polyphosphate preservatives.

Preferably, wherein a preservative is utilized herein, one or more sorbate or benzoate preservatives (or mixtures thereof) are utilized. Sorbate and benzoate preservatives suitable for use in the present invention include sorbic acid, benzoic acid, and salts thereof, including (but not limited to) calcium sorbate, sodium sorbate, potassium sorbate, calcium benzoate, sodium benzoate, potassium benzoate, and mixtures thereof. Sorbate preservatives are particularly preferred. Potassium sorbate is particularly preferred for use in the present invention.

Wherein a composition comprises a preservative, the preservative is preferably included at levels from about 0.0005% to about 0.5%, more preferably from about 0.001% to about 0.4% of the preservative, still more preferably from about 0.001% to about 0.1%, even more preferably from about 0.001% to about 0.05%, and most preferably from about 0.003% to about 0.03% of the preservative, by weight of the composition. Wherein the composition comprises a mixture of one or more preservatives, the total concentration of such preservatives is preferably maintained within these ranges.

Acidulants

If desired, the present compositions may optionally comprise one or more acidulants. An amount of an acidulant may be used to maintain the pH of the composition. Compositions of the present invention preferably have a pH of from about 2 to about 8, more preferably from about 2 to about 5, even more preferably from about 2 to about 4.5, and most preferably from about 2.7 to about 4.2. Beverage acidity can be adjusted to and maintained within the requisite range by known and conventional methods, e.g., the use of one or more of the aforementioned acidulants. Typically, acidity within the above recited ranges is a balance between maximum acidity for microbial inhibition and optimum acidity for the desired beverage flavor.

Organic as well as inorganic edible acids may be used to adjust the pH of the beverage. The acids can be present in their undissociated form or, alternatively, as their respective salts, for example, potassium or sodium hydrogen phosphate, potassium or sodium dihydrogen phosphate salts. The preferred acids are edible organic acids which include citric acid, malic acid, fumaric acid, adipic acid, phosphoric acid, gluconic acid, tartaric acid, ascorbic acid, acetic acid, phosphoric acid or mixtures thereof. The most preferred acids are citric and malic acids.

The acidulant can also serve as an antioxidant to stabilize beverage components. Examples of commonly used antioxidant include but are not limited to ascorbic acid, EDTA (ethylenediaminetetraacetic acid), and salts thereof.

Emulsifiers and Oils

One or more emulsifiers and/or oils may also be included in the present compositions for texture and opacity purposes. Typical emulsifiers and oils useful herein include, for example, mono-di glycerides, lecithin, pulp, cotton seed oil, and vegetable oil.

Carbonation Component

Carbon dioxide can be introduced into the water which is mixed with a beverage concentrate or into the beverage composition after dilution to achieve carbonation. The carbonated beverage can be placed into a container, such as a bottle or can, and then sealed. Any conventional carbonation methodology may be utilized to make carbonated beverage compositions of this invention. The amount of carbon dioxide introduced into the beverage will depend upon the particular flavor system utilized and the amount of carbonation desired.

Methods of Making

The present compositions are made according to methods which will be well known by the ordinarily skilled artisan. For convenience, non-limiting examples of methods of making follows.

To illustrate, the compositions of the present invention may be prepared by dissolving, dispersing, or otherwise mixing all components singularly or in suitable combinations together and in water where appropriate, agitating with a mechanical stirrer until all of the ingredients have been solubilized or adequately dispersed. Where appropriate, all separate solutions and dispersed may then be combined. When using tea extracts which typically are pH sensitive, it is important to adjust the desired pH with an acidulant and/or buffer system before adding the tea extracts to the mixture. Wherein a shelf stable composition is desired, the final mixture can optionally, but preferably, be pasteurized or filled aseptically at appropriate process conditions.

In making a beverage composition, a beverage concentrate may optionally be formed first. One method to prepare the concentrate form of the beverage composition would be to start with less than the required volume of water that is used in the preparation of the beverage composition. Another method would be to partially dehydrate the finally prepared beverage compositions to remove only a portion of the water and any other volatile liquids present. Dehydration may be accomplished in accordance with well known procedures, such as evaporation under vacuum. The concentrate can be in the form of a relatively thick liquid. A syrup is typically formed by adding suitable ingredients such as electrolytes or emulsions to the beverage concentrate. The syrup is then mixed with water to form a finished beverage or finished beverage concentrate. The weight ratio of water to syrup is typically from about 1:1 to about 5:1.

Carbon dioxide can be introduced either into the water to be mixed with the beverage concentrate, or into the drinkable beverage composition, to achieve carbonation. The carbonated beverage composition can then be stored in a suitable container and then sealed. Techniques for making and carbonating beverage embodiments of the present invention are described in the following references: L. F. Green (ed.), *Developments in Soft Drinks Technology*, Vol. 1 (Elsevier, 1978); G. S. Cattell and P. M. Davies, "Preparation and Processing of Fruit Juices, Cordials and Drinks", *Journal of the Society of Dairy Technology*; Vol. 38 (1), pp. 21–27, A. H. Varnam and J. P. Sutherland, *Beverages —Technology, Chemistry and Microbiology*, Chapman Hall, 1994; and A. J. Mitchell (ed.), *Formulation and Production of Carbonated Soft Drinks*, Blackie and Sons Ltd., 1990.

The essentially dry mixtures of the present invention can be prepared by blending the proper amounts and ratios of all the required dry ingredients together. Alternatively, the finally prepared beverage compositions can be dehydrated to give the essentially dry mixture of the beverage composition. The essentially dry mixture, either as, for example, a powder, granules or tablets, can later be dissolved in a proper amount of water, carbonated or non-carbonated, to make the final drinkable beverage or taken in conjunction with water. Alternatively, dry forms of the present invention may be incorporated in other compositions, including but not limited to cereal bars, breakfast bars, energy bars, and nutritional bars.

Other essentially dry forms include, for example, tablets, capsules, granules, and dry powders. Tablets may contain suitable binders, lubricants, diluents, disintegrating agents, coloring agents, flavoring agents, flow-inducing agents, and melting agents. Suitable carriers and excipients that may be used to formulate dry forms of the present invention are described in, for example, Rober, U.S. Pat. No. 3,903,297, issued Sep. 2, 1975. Techniques and compositions for making dry forms useful in the methods of this invention are described in the following references: H. W. Houghton (ed.), *Developments in Soft Drinks Technology*, Vol. 3,Chapter 6,(Elsevier, 1984); *Modern Pharmaceutics*, Chapters 9 and 10 (Banker & Rodes (ed.), 1979); Liberman et al., *Pharmaceutical Dosage Forms: Tablets* (1981); and Ansel, *Introduction to Pharmaceutical Dosage Forms*, 2nd Ed., (1976).

Kits of the Present Invention

The compositions of the present invention, including beverage compositions, beverage concentrates, and essentially dry compositions may be utilized in kits as described herein. The kits of the present invention comprise one or more compositions of the present invention together with information which informs a user of the kit, by words, pictures, and/or the like, that use of the kit will provide one or more general health and/or general physiological benefits including, but not limited to, energy, energy enhancement, energy maintenance (such as, for example, smooth and/or steady energy, mental alertness, and alertness without tension and/or nervousness), refreshment, satiation, and nutrition.

Methods of the Present Invention

The methods of the present invention comprise orally administering (i.e., through ingestion) a composition of the present invention to a mammal, preferably a human, to provide energy and/or mental alertness to such mammal. The compositions of the present invention are preferably ingested by consumers desiring a refreshing energy source or a means to satisfy between-meal hunger. The compositions are also preferably ingested by consumers who are performing, or have performed, strenuous work or by those consumers experiencing a depletion of energy. The compositions of this invention may also be ingested as a supplement to normal dietetic requirements for, for example, energy, nutrition, and/or hydration. Frequency of administration is not limited, however, such administration is typically at least once weekly, more preferably at least 3 times weekly, and most preferably at least once daily.

As used herein, the term "orally administering" with respect to the mammal (preferably, human) means that the mammal ingests or is directed to ingest (preferably, for the purpose of providing energy and/or mental alertness) one or more compositions of the present invention. Preferably, the composition is a beverage composition, concentrate, or essentially dry composition as has been described herein. Wherein the mammal is directed to ingest one or more of the compositions, such direction may be that which instructs and/or informs the user that use of the composition may and/or will provide one or more general health and/or general physiological benefits including, but not limited to, energy, energy enhancement, energy maintenance (such as, for example, smooth and/or steady energy, mental alertness, and alertness without tension and/or nervousness), refreshment, satiation, and nutrition. For example, such direction may be oral direction (e.g., through oral instruction from, for example, a physician, health professional, sales professional or organization, and/or radio or television media (i.e., advertisement) or written direction (e.g., through written direction from, for example, a physician or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a package containing the composition). As used herein, "written" means through words, pictures, symbols, and/or other visible descriptors. Such direction need not utilize the actual words "energy", "mental alertness", "human", or "mammal" but rather use of words, pictures, symbols, and the like conveying the same or similar meaning are contemplated within the scope of this invention.

Analytical Methods

Blood glucose measurements over time may be obtained to determine the provision and/or maintenance of a composition herein using any of a variety of known methods. See e.g., Gomes et al., "Anti-hyperglycemic Effect of Black Tea (Camellia sinensis) in Rat", *Journal of Ethnopharmacology*, Vol. 45, pp. 223–226 (1995) and Pizziol et al., "Effects of Caffeine on Glucose Tolerance: A Placebo-Contolled Study", *European Journal of Clinical Nutrition*, Vol. 52, pp. 846–849 (1998).

Additionally and most preferably, as used herein, the term "providing mental alertness", "energy", or the like (herein collectively referred to as mental alertness for simplicity) means to enhance the perception of mental alertness and/or energy in a consumer as described herein. Such enhancement may be measured by any of a variety of methods well-known in the art, however, the preferred method is a method as set forth herein below. This method is referred to herein for simplicity as the "Evaluation Method." The Evaluation Method is similar to the widely-accepted and statistically validated "Profile of Mood States" analytical method and has been modified to measure the perceptions of interest herein, using a test beverage composition, a control (placebo) beverage composition, and a reference beverage composition. See, McNair et al., "EITS Manual for the Profile of Mood States", published by the Education and Industrial Testing Service, 1981. A non-limiting example of the Evaluation Method is performed as follows:

The effect of a beverage composition of the present invention on mental alertness is measured using, for example, 60 human subjects (for example, 30 males and 30 females). The subjects report to a testing facility on three occasions, wherein the second occasion occurs 48 hours after the first occasion, and the third occasion occurs 48 hours after the second occasion. The subject should report to the testing facility during "low energy" times of day, i.e., from about 1 PM to about 4 PM during the day.

During these three occasions, each subject will ingest a different beverage composition, such that on completion of the method, each subject has ingested the same three different beverage compositions. Order of ingestion for the three different beverage compositions will be randomized among all subjects, i.e., for any given subject it is not critical which beverage composition is ingested first, second, or third, relative to any other subject.

The beverage compositions tested according to the method herein are the following:

(a) a beverage composition of the present invention ("test composition");
(b) a placebo composition; and
(c) a reference composition, wherein the reference composition is, for example, a cola-flavored product.

At the start of any given occasion, the subject completes a perception questionnaire to provide a baseline reading. The perception questionnaire asks the subject whether the word "energetic" describes the manner in which the subject feels at the time of reading the word. Optionally, other words/phrases may be utilized, for example, "lively", "worn out", "alert", "fatigued", and "sluggish".

The subject is instructed to choose from 5 descriptors for the word, which are:

1) not at all
2) a little;
3) moderately;
4) quite a bit;
5) extremely.

Answers are recorded by the subject. A test administrator will assign point values to each descriptor. For example, an answer of "not at all" will receive 1 point; "a little" will receive 2 points; "moderately" will receive 3 point; "quite a bit" will receive 4 points; and "extremely" will receive 5 points.

Upon completion of this baseline, during any given occasion, a subject will then ingest one of a:

(a) 330 mL of a test composition over a ten minute period;
(b) 330 mL of a placebo composition over a ten minute period; or
(c) 12 ounces of a reference composition over a ten minute period.

After consumption of one of these compositions, a given subject will repeat a new perception questionnaire at various time points. Each new perception questionnaire sets forth the same word ("energetic") and descriptors as have been described above, and the test administrator uses the same point assignment system as previously utilized. The time points are: 15, 30, 45, 60, 90, 120, 150, and 180 minutes after consumption of the composition. Point assignments will be averaged for the 15, 30, 45, 60, 90, 120, and 150 minute time points for each subject, to determine "provision of mental alertness" (the 180 minute time period is not included to discount for any "artificial" feelings of alertness and/or energy related to completion of the test). Point assignments will be averaged for the 90, 120, and 150 minute time points for each subject, to determine "maintenance of mental alertness."

On the second and third occasions, the above-described steps will be taken, wherein each subject ingests one of the three compositions not ingested on any previous occasion.

After the third occasion, student t-tests will be utilized to compare the mean normalized point averages for "provision of mental alertness" and "maintenance of mental alertness" among the three occasions. The data is normalized to account for baseline variation for each of the subjects. Based on aggregated data for each of the 60 subjects and for a given composition, ninety-five percent (95%) confidence (separately for "provision of mental alertness" and "maintenance of mental alertness") will be considered significant.

Using this Evaluation Method, the preferred test compositions herein provide and/or maintain mental alertness significantly better relative to the placebo composition and/or the reference composition.

EXAMPLES

The following are non-limiting examples of the present compositions which are prepared utilizing conventional methods. The following examples are provided to illustrate the invention and are not intended to limit the scope thereof in any manner.

EXAMPLE I

A beverage composition is prepared by combining the following components in a conventional manner:

| Component | | Wt. % |
|---|---|---|
| Glucose | | 4.000 |
| Sucrose | | 5.600 |
| Maltodextrin | | 2.000 |
| Fruit Juice Concentrate | | 2.000 |
| Dairy Base | | 5.000 |
| Pectin | | 0.150 |
| Fructo-oligosaccharides (Beghin-Meiji) | | 0.200 |
| Mate Tea Extract | | 0.025 |
| Guarana Extract | | 0.050 |
| Ascorbic Acid | (mg/100 g) | 37.920 |
| Vitamin E | (mg/100 g) | 2.440 |
| Nicotinamide | (mg/100 g) | 2.424 |
| Pantothenic Acid | (mg/100 g) | 1.212 |
| Vitamin $B_6$ | (mg/100 g) | 0.244 |
| Biotin | (mg/100 g) | 0.036 |
| Vitamin $B_{12}$ | (µg/100 g) | 0.076 |
| Citric Acid | | 0.050 |
| Sodium Citrate | | 0.100 |
| Flavors | | 0.070 |
| Water | | quantum satis |

EXAMPLE II

A beverage composition is prepared by blending the following components in a conventional manner:

| Component | Wt % |
|---|---|
| Glucose | 4.000 |
| Sucrose | 5.860 |
| Maltodextrin | 2.000 |
| Fruit Juice | 10.000 |
| Green Tea Extract | 0.120 |
| Guarana Extract | 0.060 |
| Ascorbic Acid | 0.040 |
| Sodium Citrate | 0.100 |
| Citric Acid | 0.200 |
| Flavors | 0.130 |
| Water | quantum satis |

EXAMPLE III

A beverage concentrate is prepared by blending the following components in a conventional manner:

| Ingredients | Wt % |
|---|---|
| Glucose | 16.000 |
| Sucrose | 10.000 |
| Maltodextrin | 16.000 |
| Fruit Juice Concentrates | 5.000 |
| Dairy Base | 30.000 |
| Pectin | 1.200 |
| Fructo-oligosaccharides (Beghin-Meiji) | 2.000 |
| Mate Extract | 0.200 |
| Guarana Extract | 0.340 |
| Ascorbic Acid | 0.210 |
| Citric Acid | 0.533 |
| Sodium Citrate | 0.700 |
| Aspartame | 0.035 |
| Acesulfame K | 0.070 |
| Flavors | 0.489 |
| Water | quantum satis |

EXAMPLE IV

A essentially dry composition is prepared by blending the following components in a conventional manner:

| Component | Wt. % |
|---|---|
| Glucose | 33.700 |
| Sucrose | 32.500 |
| Maltodextrin | 17.500 |
| Dairy Base | 10.000 |
| Pectin | 0.900 |
| Fructo-oligosaccharides (Beghin-Meiji) | 1.700 |
| Mate Extract | 2.000 |
| Guarana Extract | 0.400 |
| Ascorbic Acid | 0.300 |
| Citric Acid | 0.425 |
| Sodium Citrate | 0.290 |
| Flavors | 0.285 |

EXAMPLE V

A beverage concentrate is prepared by blending the following components in a conventional manner:

| Component | Wt. % |
|---|---|
| Water | quantum satis |
| Milk | 50 |
| Fructose | 1 |
| Sucrose | 1 |
| Maltodextrin | 1.5 |
| Acesulfame K | 0.015 |
| Simplesse 100 (Kelco Nutra Sweet Co., Chicago, IL) | 3 |
| Green Tea Powder | 0.15 |
| Vanilla | 0.60 |
| Vitamins | 0.05 |
| Caffeine | 0.012 |
| Coffee Extract | 2.5 |
| Carrageenan, xanthan, and guar gums | 0.05 |
| Sucrose Esters | 0.2 |

EXAMPLE VI

A beverage concentrate is prepared by blending the following components in a conventional manner:

| Component | Wt. % |
|---|---|
| Water | quantum satis |
| Milk | 50 |
| Fructose | 1 |
| Sucrose | 1 |
| Maltodextrin | 1.5 |
| Acesulfame K | 0.015 |
| Simplesse 100 (Kelco Nutra Sweet Co., Chicago, IL) | 3 |
| Green Tea Powder | 0.15 |
| Vanilla | 0.45 |
| Vitamins | 0.04 |
| Toddy (7.5% sol) Coffee Extract | 4.31 |
| Instant Coffee Powder | 0.4 |
| Carrageenan, xanthan, and guar gums | 0.05 |

What is claimed is:

1. A beverage composition comprising:
 (a) from about 0.1% to about 15% of one or more monosaccharides, by weight of the composition;
 (b) from about 0.1% to about 15% o f one or more disaccharides, by weight of the composition ;
 (c) from about 0.1% to about 15% of maltodextrin, by weight of the composition;

(d) one or more soluble fibers; and (e) more than about 60% water;

wherein the ratio of monosaccharide to maltodextrin is from about 1:5 to about 10:1, by weight.

2. A beverage composition according to claim 1 comprising:
   (a) from about 1% to about 5% of one or more monosaccharides, by weight of the composition, wherein the monosaccharides are selected from the group consisting of glucose and fructose;
   (b) from about 1% to about 8% sucrose, by weight of the composition;
   (c) from about 1% to about 5% of the maltodextrin, by weight of the composition; and
   (d) from about 0.01% to about 15% of the soluble fiber, by weight of the composition.

3. A beverage composition according to claim 2 comprising:
   (a) from about 1% to about 5% glucose, by weight of the composition;
   (b) from about 1% to about 8% sucrose, by weight of the composition; and
   (c) from about 1% to about 5% of the maltodextrin, by weight of the composition.

4. A beverage composition according to claim 3 wherein the ratio of monosaccharide to maltodextrin is from about 1:2 to about 3:1, by weight of the composition.

5. A beverage composition according to claim 3 wherein the soluble fiber is selected from the group consisting of pectins, psyllium, guar gum, xanthan, alginates, gum arabic, fructo-oligosaccharides, inulin, agar, carrageenan, and mixtures thereof.

6. A beverage composition according to claim 5 wherein the soluble fiber is selected from the group consisting of guar gum, xanthan, carrageenan, psyllium, fructo-oligosaccharides. and mixtures thereof.

7. A beverage composition of claim 5 wherein the soluble fiber is a fructo-oligosaccharide.

8. A beverage composition according to claim 5 further comprising from about 0.01% to about 15% of milk base solids, by weight of the composition.

9. A beverage composition according to claim 8 comprising from about 0.1% to about 5% of milk base solids, by weight of the composition.

10. A beverage composition according to claim 9 having a ratio of total soluble fibers to total milk base solids of from about 2:1 to about 1:6, by weight of the composition.

11. A beverage composition according to claim 2 further comprising one or more bracers.

12. A beverage composition according to claim 11 wherein at least one bracer is caffeine.

13. A beverage composition according to claim 12 wherein the caffeine is at least partially obtained from a botanical present in the composition; wherein the botanical is selected from the group consisting of green tea, guarana, mate', black tea, cola nut, cocoa, coffee, and mixtures thereof.

14. A beverage composition according to claim 13 comprising from about 0.005% to about 0.05% caffeine, by weight of the composition.

15. A beverage composition according to claim 14 comprising from about 0.005% to about 0.02% caffeine, by weight of the composition.

16. A beverage composition according to claim 11 further comprising at least about 0.01% of one or more flavanols, by weight of the composition.

17. A beverage composition according to claim 16 comprising from about 0.01% to about 0.05% of one or more flavanols, by weight of the composition.

18. A beverage composition according to claim 16 wherein the bracer is caffeine; and wherein the ratio of caffeine to flavanol is from about 1:0.5 to about 1:30, by weight of the composition.

19. A beverage composition according to claim 18 wherein the ratio of caffeine to flavanol is from about 1:1 to about 1:30, by weight of the composition.

20. A beverage composition according to claim 19 further comprising one or more botanicals selected from the group consisting of tea, aloe vera, guarana, ginseng, ginkgo, hawthorn, hibiscus, rose hips, chamomile, peppermint, fennel, ginger, licorice, lotus seed, schizandra, saw palmetto, sarsaparilla, safflower, St. John's Wort, curcuma, cardimom, nutmeg, cassia bark, buchu, cinnamon, jasmine, haw, chrysanthemum, water chestnut, sugar cane, lychee, bamboo shoots, vanilla, coffee, and mixtures thereof.

21. A beverage composition according to claim 20 wherein the botanicals are selected from the group consisting of tea, guarana, ginseng, ginko, coffee, and mixtures thereof.

22. A beverage composition according to claim 21 further comprising at least one nutrient.

23. A beverage composition according to claim 22 wherein at least one nutrient is selected from the group consisting of vitamin C, vitamin $B_6$, vitamin $B_{12}$, vitamin E, pantothenic acid, niacin, and biotin.

24. A beverage composition according to claim 1 comprising:
    (a) from about 0.01% to about 15% of the soluble fiber; and
    (b) from about 0.01% to about 15% milk base solids.

25. A kit comprising:
    (a) a composition according to claim 1; and
    (b) information that use of the composition provides one or more benefits selected from the group consisting of general health benefits and general physiological benefits.

26. A kit according to claim 25 wherein at least one of the benefits is selected from the group consisting of energy and mental alertness.

27. A method of providing or maintaining mental alertness to a mammal comprising administering to the mammal a composition according to claim 1.

28. A beverage concentrate comprising:
    (a) one or more monosaccharides;
    (b) one or more disaccharides;
    (c) one or more complex carbohydrates;
    (d) from about 0.004% to about 1.4% of one or more bracers, by weight of the concentrate;
    (e) at least about 0.07% of one or more flavanols, by weight of the concentrate;
    (f) one or more soluble fibers; and
    (g) from about 20% to about 60% water;
wherein the ratio of monosaccharide to complex carbohydrate is from about 1:5 to about 10:1 and the ratio of monosaccharide to disaccharide is from about 1:15 to about 15:1, by weight of the concentrate.

29. A beverage concentrate according to claim 28 further comprising one or more milk base solids.

30. A beverage concentrate according to claim 29 wherein the soluble fiber is selected from the group consisting of pectins, psyllium, guar gum, xanthan, alginates, gum arabic, fructo-oligosaccharides, inulin, agar, carrageenan, and mixtures thereof.

31. A beverage concentrate according to claim 30 wherein the soluble fiber is a fructo-oligosaccharide.

32. A kit comprising:
(a) a composition according to claim 28; and
(b) information that use of the composition provides one or more benefits selected from the group consisting of energy and mental alertness.

33. An essentially dry composition comprising:
(a) one or more monosaccharides;
(b) one or more disaccharides; and
(c) one or more complex carbohydrates;
(d) one or more soluble fibers; and
(e) less than about 20% water;
wherein the composition has a ratio of monosaccharide to complex carbohydrate of from about 1:5 to about 10:1 and a ratio of monosaccharide to disaccharide of from about 1:15 to about 15:1, by weight of the composition.

34. A composition according to claim 33 further comprising from about 0.004% to about 1.4% of one or more bracers, by weight of the composition.

35. A composition according to claim 34 further comprising at least about 0.07% of one or more flavanols, by weight of the composition.

36. A composition according to claim 35 further comprising one or more soluble fibers and one or more milk base solids; wherein the composition has a ratio of total carbohydrates to total soluble fibers of from about 100:1 to about to 1:1 and wherein the composition has a ratio of total soluble fibers to total milk base solids of from about 5:1 to about 1:20, by weight of the composition.

37. A composition according to claim 36 wherein the soluble fiber is selected from the group consisting of pectins, psyllium, guar gum, xanthan, alginates, gum arabic, fructo-oligosaccharides, inulin, agar, carrageenan, and mixtures thereof.

38. A composition according to claim 37 wherein the soluble fiber is a fructo-oligosaccharide.

39. A kit comprising:
(a) a composition according to claim 33; and
(b) information that use of the composition provides one or more benefits selected from the group consisting of energy and mental alertness.

* * * * *